(12) United States Patent
Mitsuhashi et al.

(10) Patent No.: US 9,289,127 B2
(45) Date of Patent: Mar. 22, 2016

(54) PROBE AND IMAGING APPARATUS FOR DIAGNOSIS

(75) Inventors: Kenta Mitsuhashi, Fujinomiya (JP); Ryou Nakamoto, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 350 days.

(21) Appl. No.: 13/616,814

(22) Filed: Sep. 14, 2012

(65) Prior Publication Data

US 2013/0006104 A1    Jan. 3, 2013

Related U.S. Application Data

(63) Continuation of application No. PCT/JP2010/007594, filed on Dec. 28, 2010.

(30) Foreign Application Priority Data

Mar. 30, 2010   (JP) .................................. 2010-079583

(51) Int. Cl.
*A61B 5/05*   (2006.01)
*A61B 5/00*   (2006.01)
(Continued)

(52) U.S. Cl.
CPC ............. *A61B 5/0066* (2013.01); *A61B 5/0084* (2013.01); *A61B 1/00121* (2013.01); *A61B 1/00142* (2013.01); *A61B 8/12* (2013.01); *A61B 2562/225* (2013.01)

(58) Field of Classification Search
None
See application file for complete search history.

(56) References Cited

U.S. PATENT DOCUMENTS

| 4,030,494 A | 6/1977 | Tenczar |
| 5,352,210 A | 10/1994 | Marrucchi |

(Continued)

FOREIGN PATENT DOCUMENTS

| JP | 57-66731 A | 4/1982 |
| JP | 1-250919 A | 10/1989 |

(Continued)

OTHER PUBLICATIONS

Extended European Search Report dated Feb. 19, 2014, issued by the European Patent Office in corresponding European Patent Application No. 10848877.6. (7 pgs).

(Continued)

*Primary Examiner* — James Kish
*Assistant Examiner* — Shahdeep Mohammed
(74) *Attorney, Agent, or Firm* — Buchanan Ingersoll & Rooney PC

(57) ABSTRACT

A probe includes a connector having a connection end surface, a first cover covering the connection end surface of the connector and defined by a surface perpendicular to a first direction corresponding to the direction toward which the probe is inserted, and a second cover configured to move in a second direction corresponding to a direction opposite to the first direction and which covers the connector by being stretched from the outer circumference of the first cover toward the second direction. The second cover moves in the second direction by receiving a press force directed toward the second direction from a wall surface formed by an opening of the adapter unit at the time of insertion of the connector into the adapter unit. The first cover is configured to be broken by the connector's press force directed in the first direction when the second cover moves in the second direction.

10 Claims, 9 Drawing Sheets

(51) Int. Cl.
*A61B 8/12* (2006.01)
*A61B 1/00* (2006.01)

(56) References Cited

U.S. PATENT DOCUMENTS

| | | |
|---|---|---|
| 5,431,641 A | 7/1995 | Grözinger et al. |
| 2002/0133058 A1* | 9/2002 | Calderwood ................ 600/122 |
| 2003/0216723 A1 | 11/2003 | Shinmura et al. |
| 2004/0049111 A1* | 3/2004 | Hirooka et al. .............. 600/437 |
| 2005/0168751 A1* | 8/2005 | Horii et al. ................... 356/479 |
| 2006/0173483 A1* | 8/2006 | Kieturakis et al. ........... 606/192 |
| 2008/0283770 A1* | 11/2008 | Takahashi ................. 250/458.1 |
| 2010/0200261 A1 | 8/2010 | Boutot |

FOREIGN PATENT DOCUMENTS

| | | |
|---|---|---|
| JP | 3-275030 A | 12/1991 |
| JP | 2003-325543 A | 11/2003 |
| JP | 2005-196080 A | 7/2005 |
| JP | 2006-204605 A | 8/2006 |
| JP | 2009-240711 A | 10/2009 |
| WO | 2009/044029 A2 | 4/2009 |

OTHER PUBLICATIONS

International Search Report (PCT/ISA/210) issued on Jan. 25, 2011, by the Japanese Patent Office as the International Searching Authority for International Application No. PCT/JP2010/007594.

Chinese Office Action dated May 30, 2014, issued in corresponding Chinese Patent Application No. 201080066027. (2 pgs).

* cited by examiner

FIG. 3A
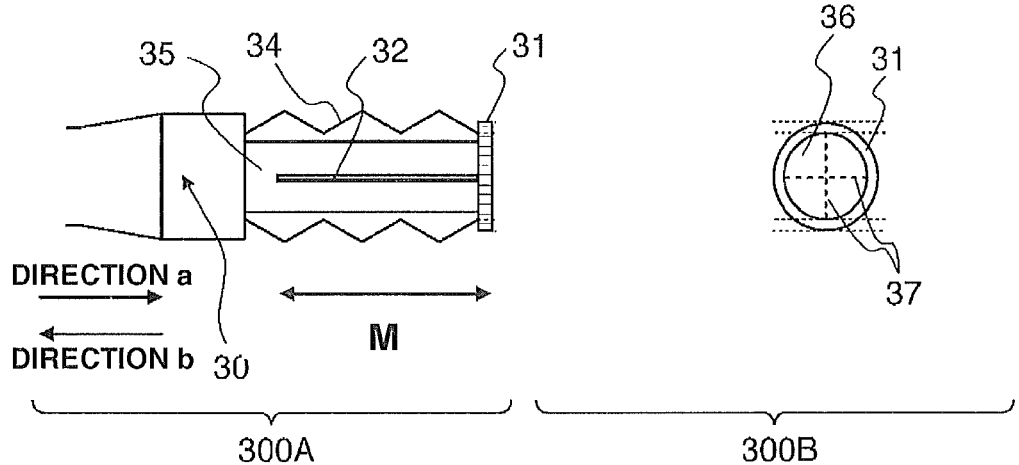
FIG. 3B
FIG. 3C
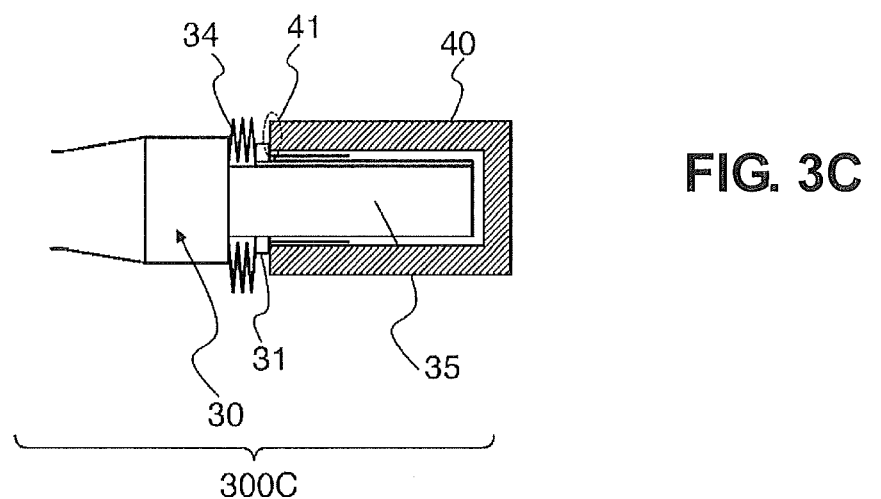

DIRECTION a
DIRECTION b

DIRECTION a
DIRECTION b

DIRECTION a ↑
DIRECTION b ↓

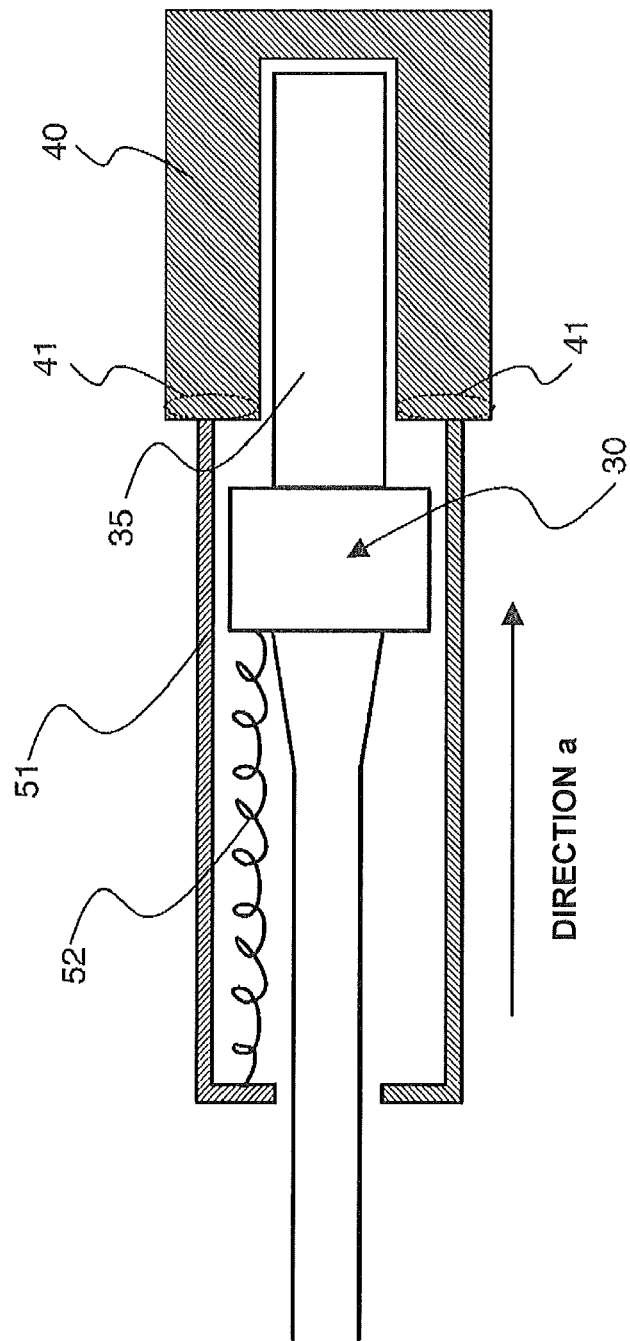

PROBE AND IMAGING APPARATUS FOR DIAGNOSIS

CROSS REFERENCE TO RELATED APPLICATION

This application is a continuation of International Application No. PCT/JP2010/007594, filed on Dec. 28, 2012, which claims priority to Japanese Patent Application JP2010-079583 filed in Japan on Mar. 30, 2010, the entire content of both of which is incorporated herein by reference.

TECHNOLOGICAL FIELD

The disclosure here generally involves a probe and an imaging apparatus for diagnosis.

BACKGROUND DISCUSSION

In the past, an optical coherent tomography imaging apparatus for diagnosis (OCT) (for example, see Japanese Unexamined Patent Publication No. 2005-196080) or an optical frequency domain imaging (OFDI) apparatus utilizing wavelength sweep, which is an improved type of OCT, has been widely utilized for diagnosis before an operation through treatment inside a blood vessel with a high functional catheter such as a balloon catheter, a stent or the like, or for a result confirmation after an operation (hereinafter, in this disclosure, the optical coherent tomography imaging apparatus for diagnosis (OCT) and the optical frequency domain imaging (OFDI) apparatus utilizing wavelength sweep will be generically referred to as "imaging apparatus for diagnosis").

In the imaging apparatus for diagnosis, an optical probe unit includes an imaging core having an optical lens and an optical mirror (transmitting and receiving unit). When a measurement is being made (for example, a diagnosis), the optical probe unit is inserted inside a blood vessel and, while rotating the imaging core with a scanner and pull-back unit (adapter apparatus), a measurement light is emanated from the transmitting and receiving unit at the distal end into the blood vessel and concurrently, reflected light from the biological tissue is light-received. Thus, a radial scan inside the blood vessel is carried out. Then, interference light is generated by making the afore-mentioned light-received reflected-light and the reference light interfere with each other such that a tomographic image of the blood vessel is visualized based on the afore-mentioned interference light. With respect to the imaging apparatus for diagnosis, there is also known an apparatus using ultra-sound or other imaging technologies other than the system using light mentioned above.

The optical probe unit is provided with a connector to be connected to the scanner and pull-back unit. In the optical probe unit, a signal (light, electrical signal) is received from the scanner and pull-back unit through the connector. Therefore, it is necessary to prevent the connector from becoming dirty as would be caused by a foreign matter such as liquid (for example, blood, saline), dust or the like becoming attached or contacting the connector.

In case of a situation in which the connector has become dirty and has become wet due to foreign matters such as a liquid, i.e., blood, saline or the like, or dust and the like, there is a possibility that the following problems or similar such problems may be caused.
1. Electric Shock to Patient
2. Contamination of Optical Probe Unit
3. Rust and/or Corrosion of Scanner and Pull-back Unit
4. Attenuation of Signal (Optical Loss, etc.)

In order to remedy the above issues, there is known a technology in which the connection end surface of the connector is protected by using a cap or the like which is formed by plastic, a flexible resin or similar material. However, even if protecting the connection end surface by using such a cap, if the operator's hand becomes wet such as caused by saline, blood or the like when the operator disengages the cap, there is a possibility that the connection end surface of the connector will become wet.

More specifically, even if the connection end surface of the connector is protected by a cap, it is possible for the operator to easily touch the connector, so that there is still a risk that the connection end surface will become dirty from a foreign matter such as blood, saline, etc.

SUMMARY

The probe disclosed here is configured so that the operator is inhibited or prevented from easily touching the connector and so the connector is not so likely to become wet or dirty, or otherwise soiled.

One embodiment of the probe disclosed here is a probe to be inserted inside a body-cavity and includes: a connector inserted into an adapter unit provided in an imaging apparatus for diagnosis which photographs a tomographic image inside the body-cavity and whose end portion defines a connection end surface; a first cover for covering the side of the connection end surface of the connector, which is defined by a surface perpendicular to a first direction expressing the direction in which the probe is inserted; and a second cover which is movable in a second direction expressing the direction opposite to the first direction and which covers the connector by being stretched from the outer circumference of the first cover toward the second direction. The probe is configured such that the second cover moves toward the second direction by receiving a press force directed toward the second direction from a wall surface formed by an opening of the adapter unit at the time of insertion of the connector into the adapter unit, and the first cover is to be broken by the connector's press force directed toward the first direction in a case in which the second cover moves toward the second direction.

With this construction, it is not so easy for the operator to touch the connector. This desirably helps prevent the connector from becoming wet or dirty or similarly soiled or contaminated.

Other features and aspects of the probe disclosed here by reference to an illustrated and described example will become clear from the following explanation with reference to the attached drawings. In the attached drawings, the same reference numerals are used to identify the same or similar features.

BRIEF DESCRIPTION OF DRAWINGS

FIG. 3A is a schematic view showing a first example of a cross section of a connection connector unit shown in FIG. 2.

FIG. 3B is a schematic end view showing one example of a connection connector unit shown in FIG. 2.

FIG. 3C is a further schematic view showing a first example of a cross section of a connection connector unit shown in FIG. 2.

FIG. 7C is a further schematic view showing the connection connector unit of the second embodiment.

DETAILED DESCRIPTION

Figure 1:
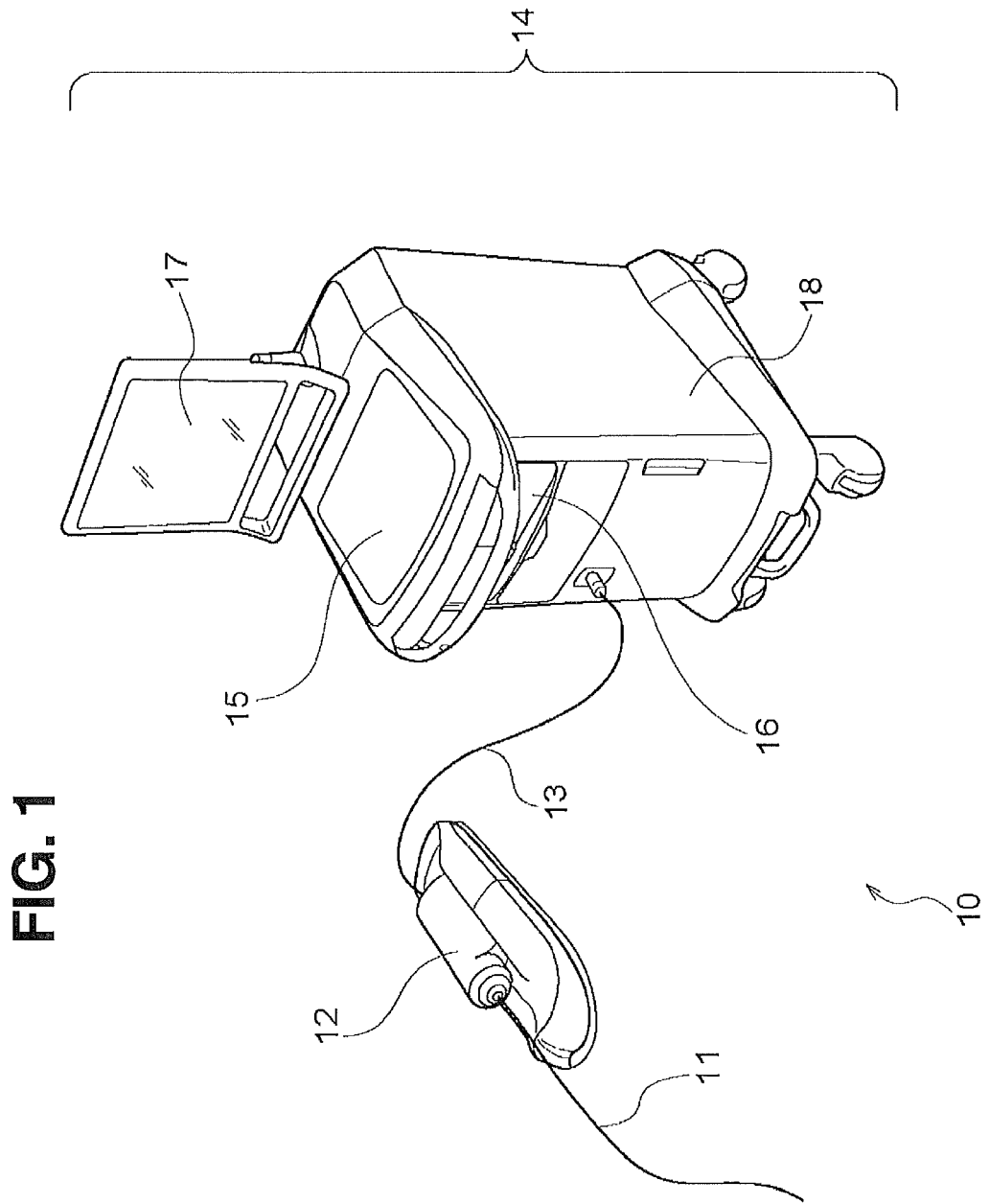
FIG. 1 is a schematic view showing one example of an imaging apparatus for diagnosis according to one embodiment of the disclosure described by way of example.

FIG. 1 schematically illustrates an example of an exterior construction of an imaging apparatus for diagnosis (optical coherent tomography imaging apparatus for diagnosis or optical frequency domain imaging apparatus utilizing wavelength sweep) 10 relating to one embodiment disclosed here by way of example.

The imaging apparatus for diagnosis 10 includes an optical probe unit 11, a scanner and pull-back unit (adapter apparatus) 12 and an operation control apparatus 14. The scanner and pull-back unit 12 and the operation control apparatus 14 are connected by means of a signal line 13.

The optical probe unit 11 is inserted inside a body-cavity such as a blood vessel or the like and measures the state inside the body-cavity. The scanner and pull-back unit 12 is detachably connected with respect to the optical probe unit 11 and controls the radial operation of an imaging core inserted inside the optical probe unit 11 by driving a built-in motor. The scanner and pull-back unit 12 is provided with an adapter unit (adapter unit 40 described later), and gives and receives various kinds of signals with respect to the optical probe unit 11 through the afore-mentioned adapter unit.

The operation control apparatus 14 is provided with a function for inputting various kinds of set values and a function for processing data obtained by the measurement and for displaying them as tomographic images.

The operation control apparatus 14 includes a main body control unit 18, a printer and DVD recorder 16 and an operation panel 15. The main body control unit 18 processes data obtained by the measurement, outputs the process result thereof and so on. The printer and DVD recorder 16 prints the process result in the main body control unit 18, stores it as data and so on. The operation panel 15 inputs various kinds of instructions from the operator to the inside of the apparatus. More specifically, the operator inputs various kinds of set values and instructions through the operation panel 15. LCD monitor 17 is a display apparatus and displays various kinds of screens for the operator. For example, the process result in the main body control unit 18 is displayed for the operator.

Figure 2:
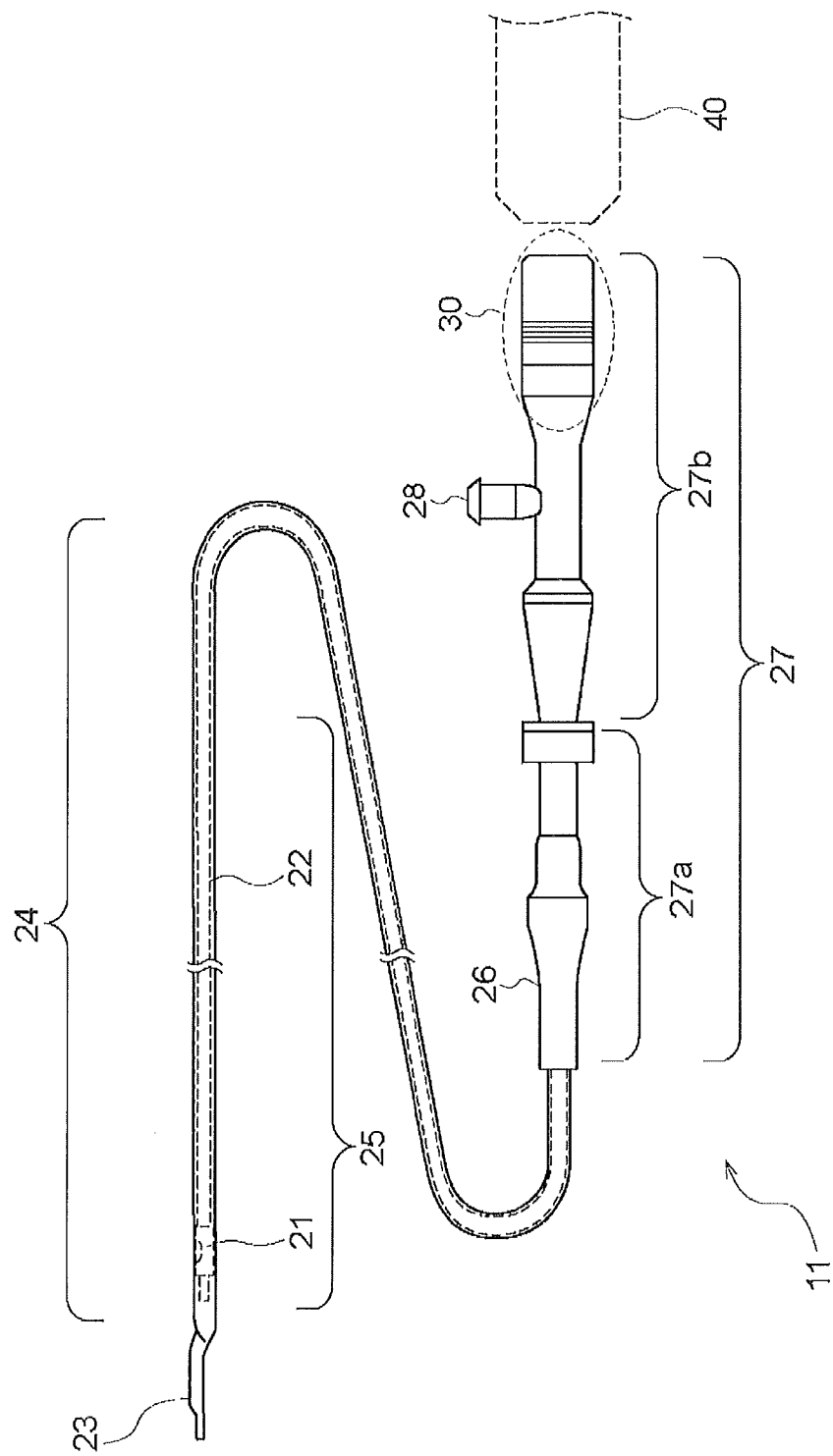
FIG. 2 is a schematic view showing one example of an optical probe unit shown in FIG. 1.

With reference also to FIG. 2, there will be explained one example of a configuration for the optical probe unit 11 shown in FIG. 1.

The optical probe unit 11 includes by a long-sized catheter sheath 24 to be inserted inside a body-cavity such as a blood vessel and the like, and a connector unit 27 which is arranged on the hand-side of a user without being inserted inside the body-cavity (in order to be operated by a user).

At the distal end of the catheter sheath 24, a tube defines a guide wire lumen 23, and the catheter sheath 24 is formed as a lumen which is continuous from a connection portion of the tube 23 for the guide wire lumen beyond a connection portion with the connector unit 27.

In the inside of a tubular lumen of a catheter sheath 24, there is inserted an imaging core 25 over approximately the full length of the catheter sheath 24. On the distal side (the side on which the tube 23 for guide wire lumen is provided) of the imaging core 25, there is provided a housing 21 which is provided with a transmitting and receiving unit for transmitting and receiving the measurement light. Also, at the imaging core 25, there is also provided a drive shaft 22 for transmitting a drive force for rotating the housing 21.

The connector unit 27 is composed of a hand-side portion 27a formed integrally at the proximal end of the catheter sheath 24 and a connection portion 27b formed integrally at the proximal end of the drive shaft 22.

At the boundary portion between the hand-side portion 27a and the catheter sheath 24, an anti-kink protector 26 is provided. Thus, a predetermined rigidity can be maintained and it is possible to prevent a bending (kink) caused by a rapid change. At the proximal end of the connection portion 27b, a connection connector 30 is provided and configured so as to be connectable with the adapter unit 40 of the scanner and pull-back unit 12.

One example of an aspect of the connection connector unit 30 is explained below with reference to FIGS. 3A-3C and FIGS. 4A-4B. Reference numeral 300A in FIG. 3A shows one example of a cross-sectional configuration of the connection connector unit 30. Reference numeral 300B in FIG. 3B shows one example of the end configuration thereof in which the ring 31 shown in FIG. 3A is seen from the direction of arrow "b". Reference numeral 300C in FIG. 3C illustrates the connection connector unit 30 when connected (coupled) with the adapter unit 40.

Figure 4A:
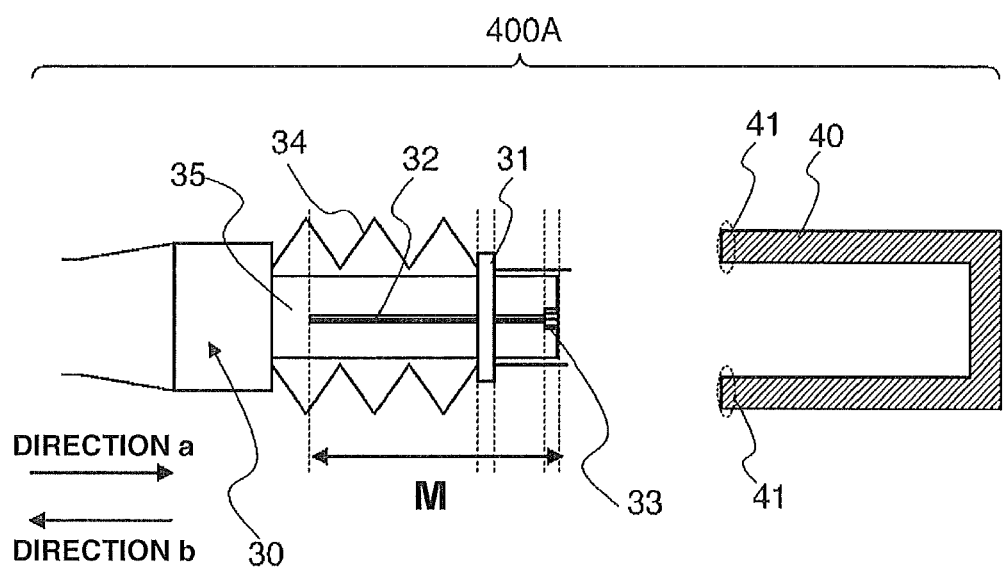
FIG. 4A is a schematic view showing one example of the connection connector unit shown in FIG. 2.
Figure 4B:
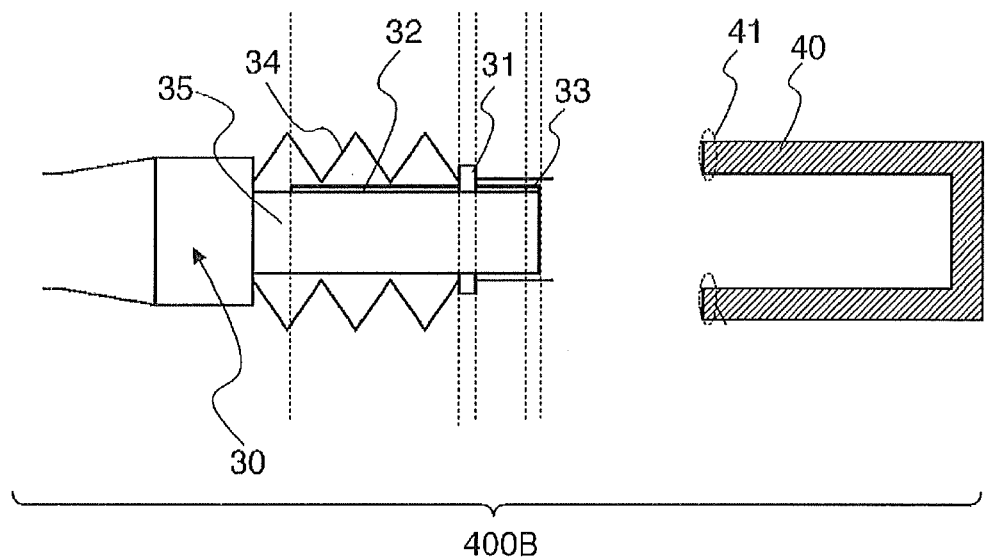
FIG. 4B is a further schematic view showing one example of the connection connector unit shown in FIG. 2.

Also, reference numeral 400A in FIG. 4A shows one example of the cross-sectional configuration in a case in which the ring 31 is moved by a predetermined distance in the direction of arrow "b" from a state shown by the reference numeral 300A in FIG. 3A, and reference numeral 400B in FIG. 4B shows one example of the cross-sectional configuration of the connection connector unit 30, as seen from the lateral direction, whereas the reference numeral 400A in FIG. 4A is supposed to be a drawing which is seen from the upper direction.

Note that the direction of arrow "a" shown in FIG. 3A and FIG. 4A indicates an insertion direction (first direction) when the connection connector unit 30 (optical probe unit 11) is inserted into the adapter unit 40, and the direction of arrow "b" shown in FIG. 3A and FIG. 4A indicates a direction (second direction opposite to the first direction) when the connection connector unit 30 (optical probe unit 11) is released from a state of being connected to the adapter unit 40.

At the connection connector unit 30, a connector 35 is provided which is actually inserted into the adapter unit 40. The connector 35 relating to this embodiment disclosed by way of example possesses a cylindrical shape.

The connector 35 includes a ring 31, a rail 32, a stopper 33, a side surface cover 34 and a connection-end surface cover 36.

The ring 31 is provided at the outer circumference of the connector 35 and has a predetermined thickness in the direction perpendicular to the peripheral surface of the connector 35. The ring 31 moves along the rail 32. More specifically, the length along the rail 32 in the direction of arrow "a" defines a movement region "M" of the ring 31.

Figure 4C:
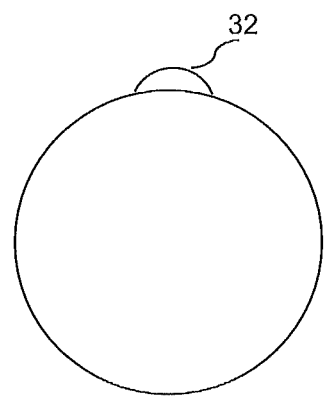
FIG. 4C is an enlarged cross-sectional view showing one example of the connector shown in FIG. 4B.

The rail 32 is provided along the direction of arrow "a" (insertion direction of the connector) on the connector 35 and plays a role in guiding the ring 31. As shown in enlarged scale in FIG. 4C, the rail 32 is formed in a convex shape.

The stopper 33 is provided at the end portion (on the connection end surface side) of the connector 35 and plays a role in preventing the ring 31 from dropping or falling off from the connector 35. The ring 31 usually receives a press force directed toward the direction of arrow "a" by the side surface cover 34 and lies in a state of being attached to the stopper 33.

The connector 35 is covered by cover members, and more specifically, the connector 35 is covered by the side surface cover 34 and a connection-end surface cover 36.

The side surface cover 34 covers the whole side surface portion of the connector 35, prevents contamination of the connector 35, and also, plays a role in preventing liquid from intruding into the connector 35. The side surface cover 34 is preferably made from a material having flexibility or elasticity such as, for example, PE, PP and silicone rubber.

The side surface cover 34 has a bellows shape and is configured to be contractible in the direction of arrow "b". With regard to the side surface cover 34, an elastic member such as a spring or the like is disposed in the inside thereof such that a press force directed in the "a" direction is applied to the ring 31. The side surface cover 34 has a relaxed or expanded state as shown by the reference numeral 300A in FIG. 3A before the connection to adapter unit 40 and obtains a state of being contracted as shown by the reference numeral 300C in FIG. 3C when the connector 35 is inserted into the adapter unit 40.

As shown by the reference numeral 300B in FIG. 3B, the ring 31 has a connection-end surface cover 36 in which perforations 37 are provided in the vertical and horizontal directions. The connection-end surface cover 36 is preferably made from a thin film such as, for example, polyethylene (PE), polypropylene (PP), polyethylene terephthalate (PET), polyvinyl chloride (PVC) and oriented polystyrene (OPS).

The connection-end surface cover 36 is broken by the connector 35, along with the movement of the ring 31 in the "b" direction, by a press force directed in the "a" direction when the connector 35 is inserted into the adapter unit 40. More specifically, when the connector 35 is inserted into the adapter unit 40, as shown by the reference numeral 300C in FIG. 3C, the ring 31 is pressed in the "b" direction by the wall surface (press portion 41) of the insertion port (opening of adapter unit 40) and the connection end-surface cover 36 is broken along the perforations 37 by the press force thereof. Also, at that time, the side surface cover 34 is contracted in the "b" direction and the connector 35 is inserted into the adapter unit 40. Note that the optical probe unit 11 is usually used once and then thrown away, so that it is not necessary for the afore-mentioned connection-end surface cover 36 to return to the original state and there is no problem in particular even if it is broken.

As explained above, according to the embodiment disclosed by way of example here, the entire surface of the connector 35 is covered by the side surface cover 34 and the connection-end surface cover 36, so that the connector 35 is never exposed to potential contaminants before the connection is made between the connection connector unit 30 and the adapter unit 40.

Therefore, when making the connection between the connector unit 30 and the adapter unit 40, the connector 35 never becomes dirty even if the operator touches a portion of the connection connector unit 30. Further, even if the side surface cover 34 becomes wet before the connection, it never happens that the inside of the adapter unit 40 gets wet.

Also, during the time when the connection connector unit 30 and the adapter unit 40 are connected, the side surface cover 34 having a bellow shape covers the connector 35 in a contracted state, so that the connector 35 is never exposed to the outside. Even when removing the connection connector unit 30 from the adapter unit 40, the side surface cover 34 returns to the original state, so that it never happens that the operator directly touches the connector 35.

Furthermore, the connection-end surface cover 36 has a structure in which it is broken when inserting the connection connector unit 30 into the adapter unit 40, so that on an occasion of the connection between the connection connector unit 30 and the adapter unit 40, the operator can accomplish the insertion directly with a single hand without touching the connection end surface or the like. Thus, it never happens that the connector 35 becomes dirty and in addition, the connector 35 can be inserted with a single hand, so that the usability thereof is also improved.

Figure 5A:
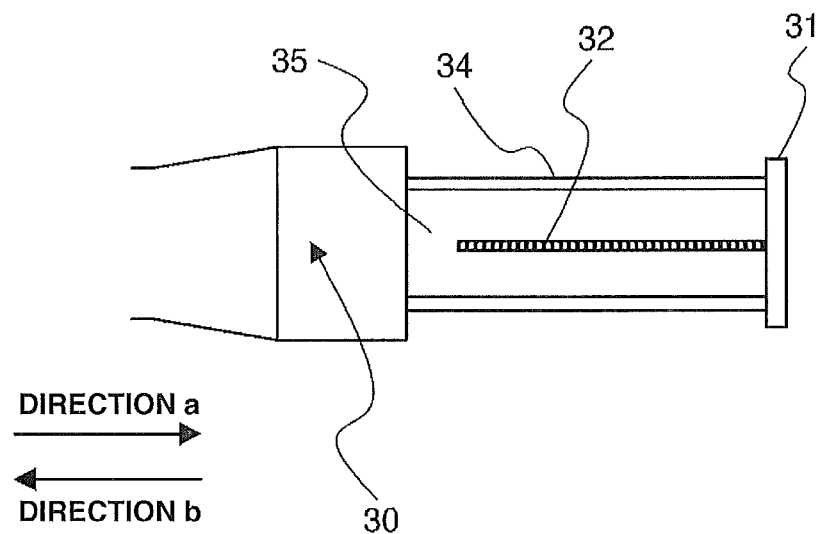
FIG. 5A is a schematic view showing a modified example of the connection connector unit of the first embodiment.

The description above describes an example of the probe disclosed here in which an elastic member is installed in the side surface cover 34 and in which the afore-mentioned cover 34 returns to the original state when removing the connection between the connection connector unit 30 and the adapter unit 40, however it is not always necessary to employ such a construction. As mentioned above, the optical probe unit 11 is usually used once and then thrown away. Hence, it is not always necessary to employ a configuration in which the elastic member is installed in the side surface cover 34 and the original state is restored when removing the connection. In this case, it is possible for the side surface cover 34 not to have a bellows shape which is, for example, shown in FIG. 5A.

Figure 5B:
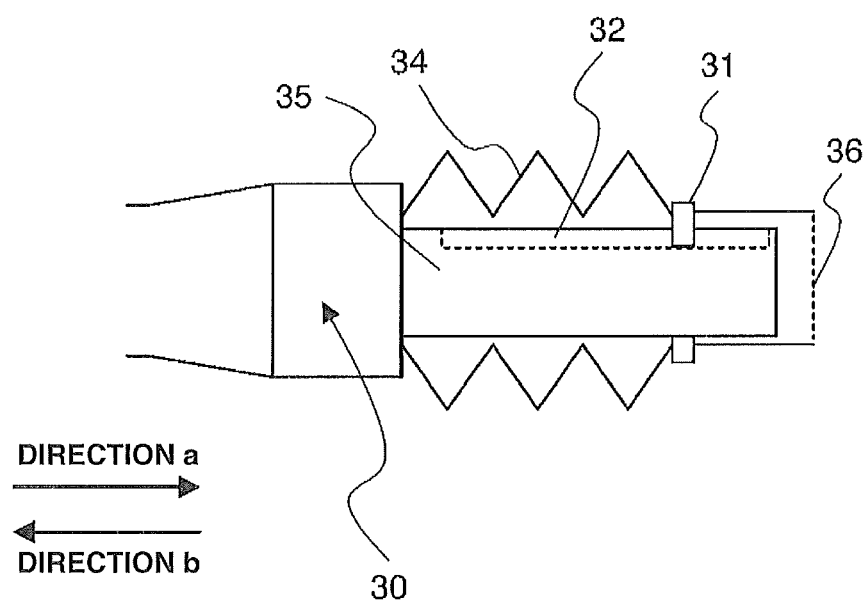
FIG. 5B is a further schematic view showing a modified example of the connection connector unit of the first embodiment.

The above-described probe representing an example of the probe disclosed here includes a stopper 33, but it is not always necessary to provide the stopper 33. For example, as shown in FIG. 5B, it is possible for the rail 32 to perform the role of the stopper by employing a construction in which the rail 32 is formed in a concave shape. Furthermore, in the explanation mentioned above, the movement of the ring 31 is guided by the rail 32, but the rail 32 is also not an indispensable element either and could be omitted.

Figure 6A:
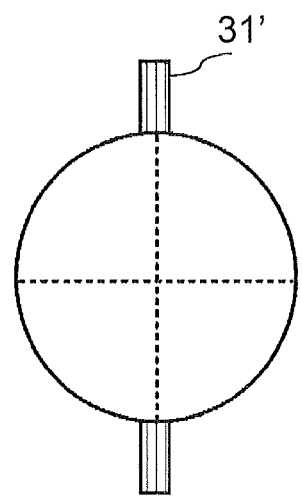
FIG. 6A is a schematic view showing a modified example of the connection connector unit of the first embodiment.
Figure 6B:
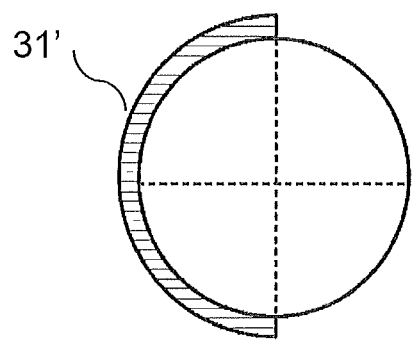
FIG. 6B is a further schematic view showing a modified example of the connection connector unit of the first embodiment.

The description above also explains that example of the probe disclosed here includes the ring 31 having a circular shape which covers the entire outer circumference of the connector 35, but it is sufficient to have a configuration in which the side surface cover 34 can be contracted in the "b" direction by a press force which is received from the wall surface (press portion 41) forming an opening of the adapter unit 40 and it is not always necessary to employ such a shape. FIG. 6A and FIG. 6B show a further embodiment of a ring 31' seen from the same direction as that of the reference numeral 300B in FIG. 3B. As shown in FIG. 6A and FIG. 6B, it is acceptable for the ring 31' to only have a thickness at a portion of the outer circumference of the connector 35.

It is also acceptable for the side surface cover 34 and the connection-end surface cover 36 to be configured as an integrated cover by using either the same material or by using different materials.

Next, there will be explained a second embodiment representing another example of the probe and diagnostic unit disclosed here. The apparatus construction and the like are similar to those of FIG. 1 and FIG. 2 which were used for explaining the first embodiment, so that the explanations thereof will be omitted and the focus here will be on explaining the difference therebetween.

Figure 7A:
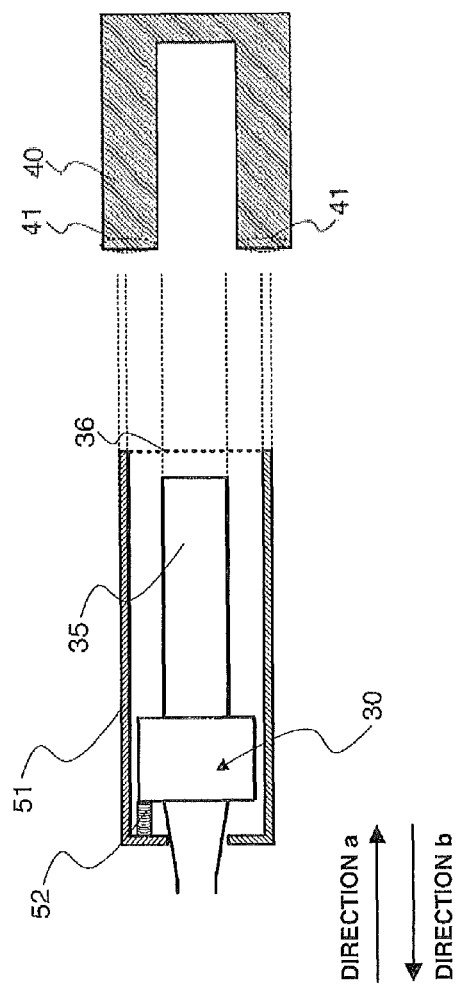
FIG. 7A is a schematic view showing a second embodiment of the connection connector unit representing another example of the disclosure here.
Figure 7B:
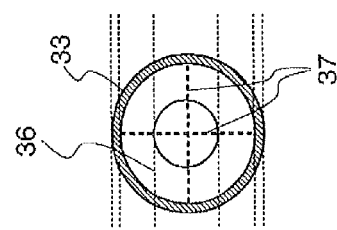
FIG. 7B is an end schematic view showing the connection connector unit of the second embodiment.

FIG. 7A-FIG. 7C are views showing one example of a connection connector unit 30 relating to the second embodiment. FIG. 7A shows one example of a cross-sectional view of the connection connector unit 30 seen from a predetermined direction, and FIG. 7C shows a view in which the connection connector unit 30 is connected (coupled) with the adapter unit 40.

Note that, similarly as in the first embodiment, the "a" direction shown in FIG. 7A and FIG. 7C shows the insertion direction (first direction) when the connection connector unit 30 (optical probe unit 11) is inserted into the adapter unit 40, and the "b" direction shown in FIG. 7A and FIG. 7C shows the direction when the connection connector unit 30 (optical probe unit 11) is released from a state of being connected to the adapter unit 40 (second direction opposite to the first direction).

At the connection connector unit 30 of the second embodiment, there are a cover 51 and an elastic member 52 provided for connector 35 which is inserted into the adapter unit 40. Note that the same reference numerals are applied to the same components as those of FIG. 3 and FIG. 4, and the explanations thereof may therefore be omitted.

Similar to the first embodiment, the connector 35 is covered by cover members having predetermined distances in the perpendicular directions from the respective portions of the connector. More specifically, the connector 35 is covered by the cover 51 and the connection end surface cover 36.

The cover 51 covers the entire side surface portion of the connector 35 to prevent dirt from coming into contact with the connector 35 and concurrently, it plays a role in preventing a liquid from intruding into the connector 35. The cover 51 has a tubular shape and is configured to be movable toward the "b" direction. On the inner wall of the cover 51, an elastic member 52 is provided, such as a spring, a rubber or the like. At the position abutting the connection end surface of the connector 35, similarly as in the first embodiment, there is provided a connection-end surface cover 36 for which perforations are provided in the vertical and horizontal directions.

The cover 51 is pressed toward the "b" direction by the wall of the end surface (press portion 41) of the adapter unit 40 when the connector 35 is inserted into the adapter unit 40. More specifically, when the connector 35 is inserted into the adapter unit 40, as shown in FIG. 7B, the cover 51 is pressed in the "b" direction by a press force of the press portion 41, the connection-end surface cover 36 is broken along the perforations and concurrently, the cover 51 moves in the "b" direction and the connector 35 is inserted into the adapter unit 40.

Also, when the connector 35 is removed from the adapter unit 40, the cover 51 returns to the original position by an action of the elastic member 52. As mentioned above, the optical probe unit 11 is usually used once and then thrown away, so that it is not always necessary to provide the elastic member 52.

According to the second embodiment, the entire surface of the connector 35 is covered by the cover 51 and the connection-end surface cover 36, so that the connector 35 is never exposed before the connection between the connection connector unit 30 and the adapter unit 40. Thus, in this case as well, an effect can be obtained similar to that for the first embodiment.

It is possible for the cover 51 and the connection-end surface cover 36 to be formed as an integrated cover by using either the same material or by using different materials.

The description above describes attributes, features and operational aspects of several examples of the probe disclosed here, but the probe is not limited by the embodiments described above and shown in the accompanying drawings, as modifications can be applied appropriately without departing from the gist thereof.

For example, in the first and second embodiments disclosed by way of example above, perforations can be formed on the connection-end surface cover 36, and the connection-end surface cover 36 can be broken along the afore-mentioned perforations when the connector 35 is inserted into the adapter unit 40. However, it is not always necessary for the connection-end surface cover 36 to have the perforations. More specifically, for this aspect of the embodiment disclosed by way of example, it is possible to employ any construction allowing for the connection-end surface cover 36 to be broken when the connector 35 is inserted into the adapter unit 40. For example, it is possible for the connection-end surface cover 36 to be formed by a thin and breakable material without providing any perforations. Also, it is possible to employ a construction in which the end portion of the connector 35 is formed as a sharpened point or shape and depending on that shape, the connection-end surface cover 36 can be broken.

Further, in the first and second embodiments mentioned above, one example of the probe was an optical probe unit connected to the imaging apparatus for diagnosis using light, but it is not limited by this aspect. For example, it is also possible to apply the construction mentioned above with respect to a probe unit connected to an imaging apparatus for diagnosis which images (generates and displays) a tomographic image of the blood vessel by utilizing ultra-sound or other imaging technologies.

The disclosure here is not to be limited by the above-mentioned embodiments, and various changes and modifications can be employed without departing from the spirit and the scope of the disclosure, as defined in the appended claims.

What is claimed is:

1. A probe to be inserted inside a body-cavity, comprising:
a connector configured to be inserted into an adapter provided in an imaging apparatus for diagnosis which visualizes a tomographic image inside the body-cavity, said connector having a connection end surface;
a first cover covering the connection end surface of the connector, the first cover defining a surface perpendicular to a first direction corresponding to a direction in which the connector is inserted; and
a second cover possessing a first axial end and a second axial end, the first axial end of the second cover being attached to the first cover, and the second axial end of the second cover being attached to the connector, second cover being movable in a second direction corresponding to a direction opposite to the first direction and covering a side of the connector,
wherein the second cover is configured to move in the second direction by receiving a press force directed toward the second direction from a wall surface formed by an opening of the adapter at the time of insertion of the connector into the adapter, and
wherein the first cover is configured to be broken by a press force of the connector directed toward the first direction when the second cover moves toward the second direction.

2. The probe according to claim 1, wherein the second cover returns from the moved position to the original position when the connector is released from a state in which the connector is connected to the adapter.

3. The probe according to claim 1, wherein the second cover comprises a plurality of contractible bellows.

4. The probe according to claim 1, wherein the second cover comprises an elastic member disposed therein.

5. The probe according to claim 1, wherein the first cover includes a plurality of perforations, the perforations being broken by the press force of the connector.

6. The probe according to claim 1, wherein the first cover is formed from a thin film.

7. The probe according to claim 1, wherein the first cover defines a connection-end surface cover and the second cover defines a side surface cover for the connector such that the entire surface of the connector is covered before being inserted into the adapter.

8. A probe to be inserted inside a body-cavity, comprising:
- a connector inserted into an an adapter provided in an imaging apparatus for diagnosis which generates and displays a tomographic image inside the body-cavity, an end portion of the connector defining a connection end surface;
- a ring provided on the connection end surface side of the connector, the ring having a predetermined thickness in a direction perpendicular to the peripheral surface of the connector and being movable in a second direction corresponding to a direction opposite to a first direction corresponding to a direction toward which the probe is inserted from the connection end surface side of the connector;
- a first cover engaged with the ring, the first cover including a surface perpendicular to the first direction and covering the connection end surface side of the connector; and
- a second cover possessing a first axial end and a second axial end, the first axial end of the second cover being attached to the ring, and the second axial end of the second cover being attached to the connector, the second cover being movable in a contractible manner in the second direction, the second cover being stretched in the second direction such that the second cover covers the connector;

wherein the ring receives a press force directed from a wall surface formed by an opening of the an adapter toward the second direction and moves together with the first cover from the connection end surface side of the connector in the second direction toward the first axial end of the second cover at a time of insertion of the connector into the an adapter, wherein the second cover contracts toward the second direction with the movement of the ring in the second direction, and wherein the first cover is configured to be broken by the connector's press force directed in the first direction when the ring moves toward the second direction.

9. The probe according to claim 8, wherein the second cover returns from the contracted state to the original state when the connector is released from the state in which the connector is connected to the adapter.

10. The probe according to claim 8, wherein:
the second cover has a bellows shape and presses the ring toward the first direction; and
the connector includes:
a stopper for preventing the ring from dropping from the connector toward the first direction, and
a rail for guiding the movement of the ring from the connection end surface side of the connector toward the second direction.

* * * * *